(12) United States Patent
Harichian et al.

(10) Patent No.: US 6,916,851 B2
(45) Date of Patent: *Jul. 12, 2005

(54) SKIN CARE COSMETIC METHODS OF SEBUM CONTROL USING CARBOXYALKYLATES OF BRANCHED ALCOHOLS AND/OR ALKOXYLATES THEREOF

(75) Inventors: Bijan Harichian, Warren, NJ (US); Carol Annette Bosko, Oradell, NJ (US); John Steven Bajor, Ramsey, NJ (US); Laurence Boen, Wayne, NJ (US); Surajit Mukherjee, Ridgewood, NJ (US)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 53 days.

This patent is subject to a terminal disclaimer.

(21) Appl. No.: 10/196,770

(22) Filed: Jul. 17, 2002

(65) Prior Publication Data

US 2004/0018948 A1 Jan. 29, 2004

(51) Int. Cl.[7] .............................................. A61K 31/26
(52) U.S. Cl. ...................... 514/559; 514/130; 514/557; 514/784; 514/785; 514/844; 514/857; 424/401; 424/70.2; 424/62; 424/63; 424/70.1; 424/78.03; 424/78.05
(58) Field of Search ................................ 514/559, 130, 514/557, 784, 785, 844, 857; 424/401, 70.2, 62, 63, 70.1, 78.03, 78.05

(56) References Cited

U.S. PATENT DOCUMENTS

| | | |
|---|---|---|
| 1,920,137 A | 7/1933 | Bruson |
| 3,992,443 A | 11/1976 | Springmann |
| 5,093,112 A | 3/1992 | Birtwistle |
| 5,328,953 A | 7/1994 | Lynch |
| 5,344,850 A | 9/1994 | Hata et al. |
| 5,756,109 A | 5/1998 | Burger et al. |
| 6,020,303 A | 2/2000 | Cripe et al. |
| 6,335,312 B1 | 1/2002 | Coffindaffer et al. |
| 6,534,073 B2 * | 3/2003 | Harichian et al. .......... 424/401 |
| 6,696,069 B2 * | 2/2004 | Harichian et al. .......... 424/401 |

FOREIGN PATENT DOCUMENTS

| | | |
|---|---|---|
| WO | 99/14180 | 3/1999 |
| WO | 99/18928 | 4/1999 |
| WO | 00/74642 | 12/2000 |

OTHER PUBLICATIONS

Harichian et al., Co–pending U.S. Appl. No. 09/872,897, filed Jun. 1, 2001; "Skin Care Cosmetic Compositions Containing Carboxymethylates of Branched Alcohols and/or Ethoxylates Thereof".

Harichian et al., Co–pending U.S. Appl. No. Unknown, filed Jul. 17, 2002; "Skin Care Cosmetic Compositions Containing Carboxyalkylates of Branched Alcohols and/or Alkoxylates Thereof".

"Antibacterial and fungicidal activites of heavy metal salts of some beta–alkyloxypropionic Acids" a lecture delivered at the 8th ISF Congress, Budapest, 1966 by Profs. Y. Abe and T. Sakurada. Keio University, Tokyo, Japan.

"Cyanoethylation of alcohols" Medyna, A.P., Volgodon, Filial, NPO "Sintez PAV", USSR, Neftepererab, Neftekhim, (Moscow) (1989)—(with Abstract).

"Alcohol Characteristics" © ExxonMobil, 2000, Rev. 2001.

* cited by examiner

Primary Examiner—Fred Krass
Assistant Examiner—Amy A. Lewis
(74) Attorney, Agent, or Firm—Ellen Plotkin

(57) ABSTRACT

Cosmetic skin care methods of using and process of making carboxyalkylates of branched alcohols and/or alkoxylates thereof and process of making same. The compounds and compositions provide control of sebum secretion from sebocytes, improved oil control and improved skin feel, prevent shine and stickiness, while also providing antimicrobial activity against bacteria associated with acne, as well as providing anti-aging benefits which results in reduced appearance of wrinkles and aged skin, improved skin color, treatment of photoaged skin, improvement in skin's radiance and clarity and finish, and an overall healthy and youthful appearance of the skin.

4 Claims, No Drawings

SKIN CARE COSMETIC METHODS OF SEBUM CONTROL USING CARBOXYALKYLATES OF BRANCHED ALCOHOLS AND/OR ALKOXYLATES THEREOF

FIELD OF THE INVENTION

Cosmetic methods and compositions for conditioning human skin by topical application to the skin of cosmetic compositions containing carboxyalkylates of branched alcohols, and/or alkoxylates thereof.

BACKGROUND OF THE INVENTION

Sebum is skin oil which is produced by sebocytes (cells of the sebaceous glands in the skin) and is then secreted to the skin surface. A frequent and undesirable skin condition is "oily skin," the condition which results from the excessive amount of sebum on the skin. Oily skin is associated with a shiny, undesirable appearance and a disagreeable tactile sensation and affects various age groups. Therefore, cosmetic products which provide both sebum control and anti-aging benefits are highly desirable.

The prior art discloses branched alcohols as compounds which provide skin benefits such as sebum suppression. For example, U.S. Pat. No. 5,756,109 issued to Burger et al. (hereinafter "Burger '109") teaches the use of a noncyclic polyunsaturated diterpene alcohol, geranyl geraniol, in combination with a retinol as a skin conditioning composition. Burger '109 discloses sebum suppression as one advantage of the branched alcohol in combination with retinol. U.S. Pat. No. 5,344,850 issued to Hata et al. discloses topical compositions containing $C_{18}$ saturated or unsaturated alcohol with four methyl branches for treating or preventing acne.

Derivatives of linear and branched alcohols have also been disclosed in the prior art for a variety of uses, ranging from industrial to personal cleansing. For example, Lynch, U.S. Pat. No. 5,328,953 relates to rubber compositions including alkoxyalkanoic acid and processes for making same; Medyna et al., "Cyanoethylation of Alcohols, *Sintez PAV* (Moscow, USSR 1989) relates to cyanoethylation of alcohols with acrylonitrile. Abe et al., "Antibacterial and Fungicidal Activities of Heavy Metal Salts of Some Beta-alkyloxypropionic Acids, "*A lecture delivered at the VIIIth I.S.F. Congress* (Budapest 1966) relates to the growth inhibiting powers of the cupric, mercuric and silver salts of certain beta-alkoxy propionic acids. WO 9918928, assigned to The Proctor & Gamble Company, discloses personal cleansing compositions comprising branched surfactant systems having a hydrophobic group and a hydrophilic group. The hydrophobic group comprises mid-chain branched and linear surfactant compounds. The hydrophilic group is selected from the group consisting of sulfate and/or ethoxylates thereof.

Springman, U.S. Pat. No. 3,992,443 (hereinafter "Springmann '443") discloses a process for the carboxymethylation of alcohols or ether alcohols in a single stage. Springmann '443 teaches the use of both straight chain and branched alcohols as suitable starting alcohols.

U.S. Pat. No. 6,020,303 issued to Cripe et al. (hereinafter "Cripe '303") discloses detergent surfactant compositions derived from mid-chain branched primary alkyl hydrophobic groups and hydrophilic groups. Specifically, Cripe '303 discloses alkyl sulfates for application in laundry and cleaning compositions. U.S. Pat. No. 5,093,112 issued to Birtwistle et al. discloses topical cleansing (detergent) compositions containing an alcohol and an alkyl or alkenyl phosphate salt.

Applicants' co-pending U.S. patent application Ser. No. 09/872,897, filed Jun. 1, 2001, discloses cosmetic methods and compositions for conditioning human skin by topical application to the skin of cosmetic compositions containing carboxymethylates of branched alcohols, and/or ethoxylates thereof. While carboxymethyl iso-alcohols are effective oil control agents, a need still exists for even more effective agents, allowing use of smaller amounts in the composition, and resulting in overall cost efficiency. A need still exists to minimize an unpleasant odor, characteristic of vinyl or a "new car smell," sometimes associated with carboxymethylates of branched alcohols, thereby making application in cosmetic skin conditioning compositions more suitable. Moreover, a need still exists for an agent with better color which, again, is more suitable for cosmetic applications.

The prior art cited above does not seem to suggest or disclose cosmetic compositions or methods for skin conditioning which avoid the shortcomings of branched alcohols and carboxymethylates thereof. Therefore, a need remains for novel compounds and cosmetic compositions that retain or enhance the beneficial effects of branched alcohols and carboxymethylates thereof in relation to sebum suppression and skin conditioning, while avoiding the unpleasant odor and water-insolubility associated with such alcohols.

SUMMARY OF THE INVENTION

Methods of using and processes for making compounds of formula A and compositions including the compounds:

$$R\text{—}O\text{-}M \qquad (A)$$

wherein:

R is a branched alkyl or alkenyl chain having at least 7 carbon atoms, and
at least two branches;
O is an oxygen atom; and
M is $(\text{—}(CH_2)_pO)_n\text{—}(CH_2)_mCO_2X)$
where n is 0 or an integer between 1 and 7, m is an integer between 2 and 4, p is an integer between 2 and 4; and X is hydrogen, a methyl group, an ethyl group, or a cation. The cation is selected from the group consisting of sodium, lithium, potassium, calcium, copper, magnesium, manganese, strontium, sulfur, zinc, and amines. Preferably, X is hydrogen or a cation.

The first step in the inventive process involves reacting a branched alcohol with acrylonitrile, followed by reacting the alkyl ether nitrile with aqueous solution of acid, such as hydrochloric acid or sulfuric acid, to form carboxyethyl iso-alcohol. The carboxyethyl iso-alcohol may further be reacted with an alcohol or base to form compound of formula A wherein the cation is selected from the group consisting of sodium, lithium, potassium, calcium, copper, magnesium, manganese, strontium, sulfur, zinc, and amines.

In another aspect, the present invention provides a process of synthesizing a compound of the formula A comprising:

(a) combining a branched alcohol with a compound selected from the group consisting of chloroacetic acid, chloropripionic acid, chlorobutyric acid, and mixtures thereof to form a heterogeneous reaction mixture; (b) stirring and heating said heterogeneous reaction mixture at slight reflux under nitrogen;(c) cooling to room temperature; (d) filtering and washing to form a paste; (e) dissolving said paste in water; (f) acidifying said dissolved paste with HCl; (g) extracting said acidified paste with chloroform or hexane; (h) removal of chloroform to form said compound of formula A.

The present invention also includes a cosmetic method of controlling or preventing an oily skin condition, especially in the facial area, by applying to the skin the inventive composition.

The invention also includes a cosmetic method of reducing, preventing or controlling sebum secretion from sebocytes by applying the inventive composition.

The invention also includes a cosmetic method of stimulating collagen synthesis by fibroblasts in the skin, by applying to the skin the inventive composition.

The inventive methods and compositions provide control of sebum secretion from sebocytes, improved oil control and improved skin feel, and prevent shine and stickiness, while also providing anti-microbial activity against bacteria associated with acne, as well as providing anti-aging benefits which result in reduced appearance of wrinkles and aged skin, improved skin color, treatment of photoaged skin, improvement in skin's radiance and clarity and finish, and an overall healthy and youthful appearance of the skin.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the oil-in-water emulsion, unless otherwise specified.

As used herein, the term "comprising" means including, made up of, composed of, consisting and/or consisting essentially of.

The term "skin" as used herein includes the skin on the face, neck, chest, back, arms, hands, legs and scalp.

Carboxyalkylates of Branched Alcohols and/or Alkoxylates Thereof

The inventive methods and compositions include a carboxyalkylate of a branched alcohol, and/or alkoxylates thereof (hereinafter "compound A"), and are of the general formula A:

$$R\text{—}O\text{-}M \quad (A)$$

wherein:
R is a branched alkyl or alkenyl chain having at least 7 carbon atoms, generally from 9 to 15 atoms, and at least two branches;
O is an oxygen atom; and
M is $(\text{—}(CH_2)_pO)_n\text{—}(CH_2)_mCO_2X)$, where n is 0 or an integer between 1 and 7, m is an integer between 2 and 4, p is an integer between 2 and 4; and X is hydrogen, a methyl group, an ethyl group, or a cation. The cation may be selected from the group consisting of sodium, lithium, potassium, calcium, magnesium, manganese, sulfur, and amines including quarternary alkyl amines and polyhydroxy amines, but is not limited thereto.

Preferably, X is a hydrogen or a cation and M is:

| | |
|---|---|
| —$CH_2CH_2CO_2X$ | (n is 0, m is 2) |
| —$CH_2CH_2CH_2CH_2CO_2X$ | (n is 0, m is 4) |
| —$CH_2CH_2O$—$CH_2CH_2CO_2X$ | (n is 1, p is 2, m is 2), or |
| —$CH_2CH_2O$—$CH_2CH_2CH_2CH_2CO_2X$ | (n is 1, p is 2, m is 4). |

More preferably, X is a hydrogen or a cation and M is:

| | |
|---|---|
| —$CH_2CH_2CO_2X$ | (n is 0, m is 2) or |
| —$CH_2CH_2O$—$CH_2CH_2CO_2X$ | (n is 1, p is 2, m is 2). |

The branched alkyl chain of the present invention is derived from a branched alcohol having 7 to 15 carbon atoms, preferably at least 9 carbon atoms and at least two branches, as noted above. The preferred alcohols from which the inventive compositions are derived contain a total of at least 10 carbon atoms in order to obtain maximum efficacy, with 13 carbon atoms most preferred. The preferred alcohols from which the inventive compositions are derived, contain from 2 to 5 branches, more preferably 3 to 4 branches, in order to maximize efficacy at minimum cost. The branches may be methyl branches, ethyl branches, or propyl branches. Preferably, the branches are methyl branches or ethyl branches, most preferably methyl branches, due to reduced odor and enhanced efficacy. The alcohol may contain a mix of various chain lengths' alcohols. Such mixed alcohol is suitable in deriving the inventive compositions, as long as the predominant alcohol (at least about 70%) in the mix contains a total of at least 7, preferably at least 9, optimally 13, carbon atoms and at least two branches.

Examples of preferred compounds of formula A are carboxyethylates of branched alcohols and/or ethoxylates thereof. The most preferred compounds of formula A are carboxyethyl tridecylisoalcohols (TDCE) and salts thereof.

Process for Carboxyethylation of Branched Alcohols

Carboxyethylates of branched alcohols may be synthesized by the following process.

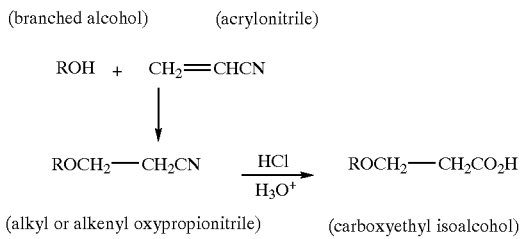

Generally, carboxyethylation of the branched alcohol involves the addition of a carboxy-ethyl group to the branched alcohol. Compound of formula A, is derived from branched alcohols which are commercially available, e.g. from Exxon or Henkel.

Step 1, etherification, involves first directly adding an acrylonitrile (available from Aldrich Chemicals) to the branched alcohol to form an alkyl or alkenyl ether nitrile, also referred to as alkyl or alkenyl oxypropionitrile. The acrylonitrile may be used in a 1:1 molar ratio to the branched alcohol, or in excess in order to drive the reaction forward and enhance yield. In one preferred embodiment, the molar ratio of branched alcohol to acrylonitrile is 1:1.5.

In the following, Step 2, the alkyl or alkenyl ether nitrile is reacted with an aqueous solution of an acid, such as hydrochloric acid or sulfuric acid, at room/ambient temperature, over potassium hydroxide or sodium hydroxide catalyst, to yield carboxyethyl isoalcohol.

The carboxyethyl isoalcohol may be further reacted with an alcohol or base, such as MeOH or NaOH, to form an R—O-M structure (A) as discussed above, such as wherein X is a methyl group or the cation sodium.

The salt forms of compound A (where M is a cation in formula A) are preferred because they are water soluble for penetration through the skin. Preferably, sodium salt is used because of commercial availability.

Tridecylcarboxyethylate, TDCE, is the most preferred carboxyalkylate of branched alcohol compound, due to water solubility and oil solubility properties which translate into effective skin activity and further to cost effectiveness due to the ability to use a smaller amount of active to gain a given degree of benefit. Additionally, TDCE has more acceptable odor and color characteristics than other similar molecules, particularly TDCM (tridecylcarboxymethylate).

Compound A of the present invention retains or ehnances the beneficial sebum suppression qualities of branched alcohols and methoxylates thereof, while eliminating the unpleasant odor and color. Moreover, compound A is an anionic surfactant, thus providing a negative charge that aids in binding the surfactant onto the skin's surface. The water soluble characteristic effectuates delivery into the skin. Moreover, as compared to prior art surfactants such as sulfate groups on branched alcohols, the carboxyl group in compound A is a better metal chelator and milder to the skin due to its relatively low acidity (pKa of approximately 3). The carboxyl group has a lower molecular weight than a sulfate group, thus lower amounts of the carboxyl group will yield more beneficial results than the sulfate group.

Compositions Including Carboxyalkylates of Branched Alcohols/Alkoxylates

Compounds of formula A are employed in the inventive methods and compositions in amounts of about 0.001% to about 50%, preferably about 0.1% to about 20%, most preferably about 0.1% to about 10%.

The inventive compositions containing compounds of formula A may also include a retinoid. Retinoids increase collagen synthesis by dermal fibroblasts. This results in protection from sun damage and smoothening of wrinkled skin. Addition of retinoids to compound A provided improved inhibition of lipogenesis as well as increased collagen synthesis in comparison to compound A alone. The term "retinoids" as used herein includes retinoic acid, retinol, retinal, and retinyl esters. Included in the term "retinoic acid" are 13-cis retinoic acid and all-trans retinoic acid.

The term "retinol" as used herein includes the following isomers of retinol: all-trans-retinol, 13-cis-retinol, 11-cis-retinol, 9-cis-retinol, 3, 4-didehydro-retinol. Preferred isomers are all-trans-retinol, 13-cis-retinol, 3,4-didehydro-retinol, 9-cis-retinol, 9-cis-retinol. Most preferred is all-trans-retinol, due to its wide commercial activity.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadecanoate, retinyl stearate, retinyl isostearate, retinyl nonadecanoate, retinyl arachidonate, retinyl behenate, retinyl linoleate, retinyl oleate, retinyl lactate, retinyl glycolate, retinyl hydroxy caprylate, retinyl hydroxy laurate, retinyl tartarate.

The retinoids in the present invention are present in an amount of from 0.001% to 10%, preferably from 0.01% to 1%, and most preferably from 0.01% to 0.05%.

Cosmetically Acceptable Vehicle

Compounds of formula A employed in the inventive methods and compositions are liquid, and thus the invention is effective even in the absence of the carrier. However, the compositions according to the invention comprise a cosmetically acceptable vehicle to act as a diluant, dispersant or carrier of compound A, so as to facilitate their distribution when the composition is applied to the skin.

The vehicle may be aqueous, anhydrous or an emulsion. Preferably, the compositions are aqueous or an emulsion, especially water-in-oil or oil-in-water emulsion. Water when present will be in amounts which may range from 5 to 99%, preferably from 40 to 90%, optimally between 60 and 90% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 and 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fafty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively, the water, solvents, silicones, esters, fafty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Additional Skin Benefit Agents

Various types of additional active ingredients may be present in cosmetic compositions of the present invention. Actives are defined as skin benefit agents other than emollients and other than ingredients that merely improve the physical characteristics of the composition. Although not limited to this category, general examples include additional anti-sebum ingredients such as talcs and silicas, as well as alpha-hydroxy acids, beta-hydroxy acids, poly-hydroxy acids, benzoyl peroxide, zinc salts, and sunscreens.

Beta-hydroxy acids include salicylic acid, for example. Zinc pyrithione is an example of zinc salts useful in the compositions of the present invention.

Sunscreens include those materials commonly employed to block ultraviolet light. Illustrative compounds are the derivatives of PABA, cinnamate and salicylate. For example, avobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation.

Many cosmetic compositions, especially those containing water, must be protected against the growth of potentially harmful microorganisms. Anti-microbial compounds, such as triclosan, and preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

Use of the Novel Compounds and Compositions

The compounds and compositions according to the invention are intended primarily as a product for topical application to human skin, especially as an agent for controlling or preventing excessive sebum secretion. Suppression of sebum provides multiple benefits, including: improved skin condition; reduction of an unpleasant appearance and feel of greasy skin; reduction and/or prevention of acne, rosacea, seborrhea, oily scalp, oily/greasy hair, and dandruff.

In use, a quantity of the composition, for example from 1 to 100 ml, is applied to exposed areas of the skin, from a suitable container or applicator and, if necessary, it is then spread over and/or rubbed into the skin using the hand or fingers or a suitable device.

The present invention also includes a cosmetic method of controlling or preventing an oily skin condition, especially in the facial area, by applying to the skin the inventive composition. In another aspect, the present invention includes a cosmetic method of controlling, preventing, or treating oily or greasy hair.

The invention also includes a cosmetic method of reducing, preventing or controlling sebum secretion from sebocytes by applying the inventive composition.

The invention also includes a cosmetic method of stimulating collagen synthesis by fibroblasts in the skin, by applying to the skin the inventive composition.

The inventive methods and compositions provide control of sebum secretion from sebocytes, improved oil control and improved skin feel, and prevent shine and stickiness, while also providing anti-microbial activity against bacteria associated with acne and, generally, controlling microbial activity of bacteria on the skin surface, as well as providing anti-aging benefits which result in reduced appearance of wrinkles and aged skin, improved skin color, treatment of photoaged skin, improvement in skin's radiance and clarity and finish, and an overall healthy and youthful appearance of the skin. Additionally, the inventive methods are useful for reducing or preventing secretion from the apocrine glands.

Product Form and Packaging

The cosmetic skin composition of the invention can be in any form, e.g. formulated as a toner, gel, lotion, a fluid cream, or a cream. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,057, incorporated by reference herein.

The following specific examples further illustrate the invention, but the invention is not limited thereto.

The branched alcohols listed in the Table below, some of which were used in the Examples, were obtained from Exxon:

TABLE 1

| Trade Name | Branching |
| --- | --- |
| Exxal ® 7 | Mixture of branched and straight chain isomers, about 40% dimethyl pentanols. |
| Exxal ® 8 | Methyl branching only, at least about 38% dimethyl hexanols. |
| Exxal ® 9 | About 33% dimethyl heptanol |
| Exxal ® 10 | Trimethyl heptanols and dimethyl octanols |
| Exxal ® 11 | About 36% dimethyl nonanol |
| Exxal ® 12 | Trimethyl nonanols |
| Exxal ® 13 | Tetramethyl nonanols and trimethyl decanols |
| Nonanol ® | About 80% 3,5,5-trimethylhexanol |
| Acropol 35 ® | About 70% $C_{13}$, about 63% dimethyl branching |

Exxal ® 13 and Acropol 35 ® are preferred alcohols, and Exxal ® 13 is the more preferred alcohol.

EXAMPLE 1

This example provided carboxymethylation of an alcohol, which yields carboxymethylates of isoalcohols with a purity of about 50% to about 70%.

Potassium tertiary-butoxide (9.42 g, 0.084 mole) was weighed out into a small round bottom flask under moisture free atmosphere ($N_2$ dry box). To this was then added 25 ml dry p-dioxane and while stirring, a mixture of Exxal® 13 alcohol 4.0 g, 0.02 mole) and chloroacetic acid (1.89 g, 0.02 mole) in 15 ml dry p-dioxane was added. The heterogeneous reaction mixture was then stirred and heated at slight reflux overnight under $N_2$. The overnight heating caused a slight coloration to the mixture. Heating was stopped and after cooling to room temperature the solids were filtered and washed with p-dioxane and suction dried to give 6.70 g lightly colored paste. The paste was dissolved in water and acidified with HCl and extracted with chloroform (separatory funnel). The chloroform was dried ($MgSO_4$) and after filtration, removal of chloroform (rotavap) yielded about 0.90 g of light brown oily liquid product. $^1H$ and $^{13}C$ NMR's of the liquid product indicated desired carboxymethylated product (acid form) ($^1H$ singlet at 4.11 ppm for R—O—$CH_2CO_2$ and multiplet at 3.56 ppm for R—$CH_2$—O—) ($^{13}C$ peaks at 60.34 and 67.88 ppm for the —$CH_2$—O—$CH_2$—CO). This was further supported by GC analysis of the liquid product (silylated) versus starting Exxal® 13 alcohol and chloroacetic acid. The carboxymethylated product had retention times of about 2 minutes and about 6 minutes longer than the alcohol and chloroacetic acid respectively. Half of the carboxymethylated product in acid form was converted to the sodium salt in water and recovery of the sodium salt form was recovered via freeze-drying. Both the acid form and the salt form of the carboxymethylated product were used in the examples that follow.

EXAMPLE 2

This example provided carboxyethylation of a branched alcohol, which yields carboxyethylates of iso-alcohols (iso-tridecyloxy propionic acid) with a purity of about 98% to about 99%.

To iso-tridecanol, Exxal® 13 alcohol (4.0 g, 0.02 mole), in a small 3-neck round bottom flask fitted with a condenser and stirrer, was added a catalytic amount of pulverized potassium hydroxide (32 milli-grams). While stirring well, acrylonitrile (0.93 g, 0.02 mole) was added dropwise via a syringe. The reaction mixture was then stirred at room/ambient temperature for two hours. During the stirring, the mixture turned warm. The mixture was then heated at 60 deg. C. for two hours. GC and IR (band at 2257 $cm^{-1}$ for CN) analyses of the reaction mixture showed the main reaction product was iso-tridecyloxypropionitrile, as well as absence of iso-tridecanol.

The iso-tridecyloxypropionitrile (2 g) and 8 ml concentrated hydrochloric acid were charged into a small 3-neck round-bottom flask fitted with a mechanical stirrer and condenser and heated at 75–80° C. (water bath) for one hour and then at reflux for 3 hours.

After allowing the reaction mixture to cool to room/ambient temperature, the aqueous layer was extracted with 20 ml chloroform and dried. Note, hexane extraction may also be used.

The chloroform was completely removed (rotavap), yielding about 2.0 g clear colorless liquid product. This was analyzed by gas chromatography (GC) and infrared spectroscopy (IR: strong carbonyl band at 1722 $cm^{-1}$) to be the carboxyethyl iso-tridecanol product. Advantageously, the purity of the carboxyethyl iso-tridecanol product is at least about 98%. Potential by products are: ammonium chloride, dimer of TDCE, ester of TDCE.

Half of the carboxyethylated product in acid form was converted to the sodium salt in water and recovery of the sodium salt form was recovered via freeze-drying.

EXAMPLE 3

This example provided comparative data on inhibition of sebocyte lipogenesis by the carboxymethylated and the carboxyethylated products of Examples 1 and 2, respectively.

The iso-tridecyl carboxymethylated product and the iso-tridecyl carboxyethylated products (hereinafter "TDCM" and "TDCE", respectively) and sodium salts thereof were obtained from Examples 1 and 2, respectively.

Secondary cultures of human sebocytes obtained from an adult male were grown in 96-well tissue culture plates (Packard Co.; Meriden, Conn.) until confluent. Sebocyte growth medium consisted of Clonetics Keratinocyte Basal Medium (KBM) supplemented with 14 µg/ml bovine pituitary extract, 0.4 µg/ml hydrocortisone, 5 µg/ml insulin, 10 ng/ml epidermal growth factor, $1.2 \times 10^{-10}$ M cholera toxin, 100 units/ml penicillin, and 100 µg/ml streptomycin. All cultures were incubated at 37° C. in the presence of 7.5% $CO_2$. Medium was changed three times per week.

On the day of experimentation, the growth medium was removed and the sebocytes washed three times with sterile Dulbecco's Modified Eagle Medium (DMEM; phenol red free). Fresh DMEM was added to each sample (duplicates, triplicates, or quadruplicates depending on the experiment) with 5 μL of test agent solubilized in ethanol or sterile, distilled water. Controls consisted of addition of ethanol alone or phenol red. Phenol Red, a known sebum suppressive agent, was employed as a positive control.

Each plate was returned to the incubator for 20 hours followed by the addition of $^{14}$C-acetate buffer (5 mM final concentration, 56 mCi/mmol specific activity). Sebocytes were returned to the incubator for four hours after which each culture was rinsed three times with phosphate buffered saline to remove unbound label. Radioactive label remaining in the sebocytes was harvested and counted using a TopCount-NXT brand scintillation counter (Packard Co., Meriden, Conn.).

The results that were obtained, expressed in terms of amount of radioactive label remaining in the sebocytes as a percent of control, are summarized in Table 2. A lower radioactive label, i.e. a lower % of control, indicates a greater inhibition of sebocyte lipogenesis.

TABLE 2

20 hour Incubation, 96 well plate

| Treatment | % of Control |
|---|---|
| Control | 100.0 |
| 100 μM Phenol Red | 46.3* |
| 1 μM Iso-tridecyl carboxymethylate | 84.8* |
| 10 μM Iso-tridecyl carboxymethylate | 43.4* |
| 100 μM Iso-tridecyl carboxymethylate | 22.8* |
| 1 μM Iso-tridecyl carboxyethylate | 48.7* |
| 10 μM Iso-tridecyl carboxyethylate | 34.6* |
| 100 μM Iso-tridecyl carboxyethylate | 11.9* |

*statistically significant at p < 0.01

As shown in Table 2, both iso-tridecyl carboxymethylate (TDCM) and iso-tridecyl carboxyethylate (TDCE) enhanced inhibition of lipogenesis at all tested concentrations. As can be seen from a comparison of the data in Table 2, TDCE performed significantly better than TDCM, i.e., TDCE was almost twice as effective as TDCM.

EXAMPLE 4

This example provides carboxypropylation of an alcohol, which yields the corresponding alkyl oxy butyric acid with a purity of about 50% to about 70%.

Potassium tertiary-butoxide (9.42 g, 0.084 mole) was weighed out into a small round bottom flask under moisture free atmosphere ($N_2$ dry box). To this was then added 25 ml dry p-dioxane or THF and while stirring, a mixture of Exxal® 13 alcohol (Branched alcohol with 13 carbons; 4.0 g, 0.02 mole) and 4-chlorobutyric acid (Aldrich Chemicals, 0.02 mole) in 15 ml dry THF was added. The heterogeneous reaction mixture was then stirred and heated at slight reflux overnight under $N_2$. Heating was stopped and after cooling to room temperature the solids were filtered and washed with THF and suction dried to give 6.70 g lightly colored paste. The paste was dissolved in water and acidified with HCl and extracted with chloroform (3×100 ml in a separatory funnel). The chloroform was dried ($MgSO_4$) and after filtration, removal of chloroform (rotavap) yielded about 1.0 g of an oily liquid product. $^1$H and $^{13}$C NMR's of the liquid product confirmed the structure of the desired $C_{13}H_{27}OCH_2CH_2CH_2CO_2H$ product (acid form).

The same or similar process is applicable for carboxyethylation, carboxybutylation, carboxypentylation, carboxyhexylation, and higher methylene groups, where, in the compound of formula A, m is an integer greater than or equal to 2. For example, for carboxyethylation, chloroacetic acid would be used with the branched alcohol.

EXAMPLE 5

This example provides a comparison of the relative activity of carboxyalkylates of the present invention with other derivatives of alcohols, as well as the branched alcohols from which the carboxyalkylates of the present invention are derived.

The experiments were conducted using the procedure set forth in the Example 3 above, with the concentrations of the compounds varied, in order to determine the concentration for each compound tested which provide a 50% sebum suppression. The concentration which provides a 50% sebum suppression relative to the control is referred to in the Table below as IC50.

The chemical structures of compounds tested, referred to by number in the Table below, are as follows.

Compound #1: ROCH2CH2CO2H (TDCE)
Compound #2: ROCH2CH2CN
Compound #3: ROCH2CH2CH2NH2
Compound #4: ROH (EXXAL 13)

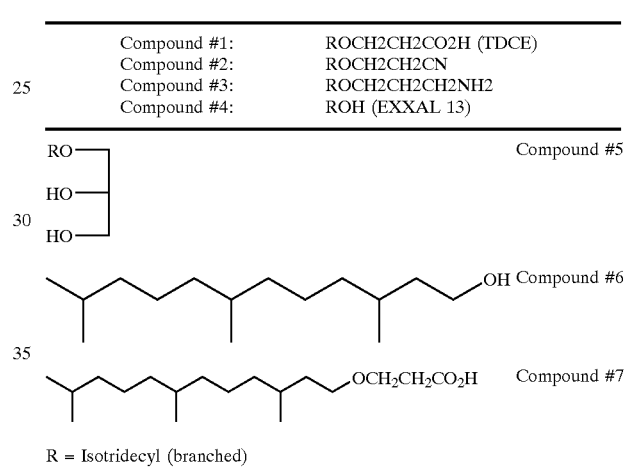

R = Isotridecyl (branched)

TABLE 3

20 hour Incubation; 96 well plate

| Compound # | Chemicals | IC 50 (micro molar) |
|---|---|---|
| 1 | C13 isoalcohol carboxyethylate (TDCE) | 5 |
| 2 | C13 isoalcohol propionitrile | >>100 |
| 3 | C13 isoalcohol oxypropyl amine | ~100 |
| 4 | C13 isoalcohol (Exxal 13) | 100 |
| 5 | C13 isoalcohol glycerol | >>100 |
| 6 | 3,7,11-trimethyl 1-dodecanol | >100 |
| 7 | 3,7,11-trimethyl 1-dodecanol carboxyethylate | 10 |

The data in this Example demonstrate the importance of the carboxyl group to the activity of the compounds as sebum suppressants. For example, the data show that TDCE (compound 1) is about 20 times as active is the branched alcohol (compound 4) from which it is derived. Compound 7 is at least about 10 times as active as the Compound 6 branched alcohol from which it is derived.

EXAMPLE 6

This example compares the color of TDCM and TDCE, showing that TDCE is better color characteristics.

The light absorbency of TDCM and TDCE compounds was determined at wavelengths of 340–500 nm using a Molecular Devices Spectramax 340 spectrophotometer. The data is shown in the Table below.

TABLE 4

| Wavelength | TDCM | TDCE | Blank |
|---|---|---|---|
| 340 | 1.459 | 0.131 | 0.093 |
| 350 | 1.014 | 0.106 | 0.073 |
| 360 | 0.692 | 0.09 | 0.06 |
| 370 | 0.482 | 0.08 | 0.053 |
| 380 | 0.336 | 0.07 | 0.045 |
| 390 | 0.251 | 0.062 | 0.039 |
| 400 | 0.197 | 0.058 | 0.037 |
| 410 | 0.161 | 0.055 | 0.037 |
| 420 | 0.138 | 0.054 | 0.036 |
| 430 | 0.124 | 0.052 | 0.036 |
| 440 | 0.097 | 0.051 | 0.035 |
| 450 | 0.078 | 0.05 | 0.035 |
| 460 | 0.069 | 0.049 | 0.035 |
| 470 | 0.064 | 0.049 | 0.036 |
| 480 | 0.058 | 0.048 | 0.035 |
| 490 | 0.054 | 0.046 | 0.034 |
| 500 | 0.051 | 0.046 | 0.035 |

The higher the number, the more light the compound absorbs at a specific wavelength, which is characteristic of a darker colors. The data show that the absorbency values for TDCM are higher than those for TDCE, indicating that TDCE is lighter in color, which is more appealing to the consumer.

EXAMPLE 7

Synthesis of Ethoxylated C13 Iso Alcohol Carboxyethylate $R(OCH2CH2)_3 CH_2CH_2CO_2H$ where $R=C_{13}$ branched Procedure:

C13 isoalcohol (22.00 g, Exxal 13) was first reacted with Thionyl chloride (excess) to form the corresponding C13 isoalcohol chloride, C13 H27Cl, in 88% yield after distilation (according to procedure outlined in Org Syn Coll Vol 4, 333, 1963).

To a reaction flask under nitrogen atmosphere containing 52.86 g (0.35 moles) of dried H(OCH2CH2)3OH (triethylene glycol, Aldrich) is added slowly 3.42 g of potasium metal. The reaction was heated at 100C for 5 hrs. The temperature of the reaction was increased to 150° C. and then the C13 H27Cl (0.073 moles) was added over 5 hrs. The reaction was cooled to room temperature and 500 ml of toluene was added. This mixture was then washed with water (3×100 ml) to remove unreacted triethylene glycol. Gas chromatography showed some formation of C13 olefin (less then 1%). The solvent was removed on a rotavap and the mixture was distilled (200–220 C.) to form the ethoxylated (3EO) C13 iso alcohol carboxyethylate in 55% isolated yield.

The same procedure is applicable to iso-alcohols of varying carbon chain lengths according to the present invention, and to alkoxylates of varying carbon chain lengths according to the present invention as disclosed above.

The 3-ethoxylated isoalcohol will be reacted with acrylonitril, followed by HCl, to form the corresponding carboxy-alkyl 3-ethoxylated isoalcohol, according to Examples 2 and 4.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic method of providing a skin benefit, the method comprising applying to the skin a composition comprising:

(i) about 0.001% to about 50% of a compound of the formula A:

$$R\text{—}O\text{-}M \quad (A)$$

wherein:

R is a branched alkyl or alkenyl chain having at least 7 carbon atoms, and at least two branches;

O is an oxygen atom; and

M is $(\text{—}(CH_2)_pO)_n\text{—}(CH_2)_mCO_2X)$, where n is 0 or an integer between 1 and 7, m is an integer between 2 and 4, p is an integer between 2 and 4;

X is hydrogen, a methyl group, an ethyl group, or a cation; and (ii) a cosmetically acceptable vehicle;

said benefit selected from the group consisting of treating and/or inhibiting:

(a) oily skin conditions;

(b) sebum secretion from sebocytes;

(c) collagen synthesis by fibroblasts in the skin; and (d) microbial activity of bacteria associated with acne.

2. The cosmetic method of claim 1, further including the skin benefit of controlling, preventing, or treating oily or greasy hair.

3. A cosmetic method of providing a skin benefit, the method comprising applying to the skin a compound of the formula A:

$$R\text{—}O\text{-}M \quad (A)$$

wherein:

R is a branched alkyl or alkenyl chain having at least 7 carbon atoms, and at least two branches;

O is an oxygen atom; and

M is $(\text{—}(CH_2)_pO)_n\text{—}(CH_2)_mCO_2X)$, where n is 0 or an integer between 1 and 7, m is an integer between 2 and 4, p is an integer between 2 and 4; and X is hydrogen, a methyl group, an ethyl group, or a cation;

said benefit selected from the group consisting of treating and/or inhibiting:

(a) oily skin conditions;

(b) sebum secretion from sebocytes;

(c) collagen synthesis by fibroblasts in the skin; and (d) microbial activity of bacteria associated with acne.

4. The cosmetic method of claim 3, further including the skin benefit of controlling, preventing, or treating oily or greasy hair.

* * * * *